United States Patent [19]

Powers

[11] Patent Number: 5,610,297

[45] Date of Patent: *Mar. 11, 1997

[54] PEPTIDES KETOAMIDES

[75] Inventor: James C. Powers, Atlanta, Ga.

[73] Assignee: Georgia Tech Research Corp., Atlanta, Ga.

[*] Notice: The term of this patent shall not extend beyond the expiration date of Pat. No. 5,514,694.

[21] Appl. No.: 539,946

[22] Filed: Oct. 6, 1995

Related U.S. Application Data

[63] Continuation of Ser. No. 247,081, May 20, 1994, abandoned, which is a continuation of Ser. No. 118,997, Sep. 9, 1993, abandoned, which is a continuation of Ser. No. 815,073, Dec. 27, 1991, abandoned.

[51] Int. Cl.$^6$ .................................................. C07D 265/30
[52] U.S. Cl. ..................... 544/168; 548/496; 548/535; 548/312.7; 548/314.7; 548/953; 560/32; 560/38; 560/40; 560/41; 560/45; 560/125; 560/159; 560/169; 564/153; 564/157; 564/159; 546/210; 546/207; 546/201; 546/268.1; 546/272.7; 546/277.4; 546/279.1
[58] Field of Search ................... 560/32, 38, 40, 560/41, 45, 125, 159, 169; 548/334, 496, 535; 544/168; 564/153, 157, 159

[56] References Cited

U.S. PATENT DOCUMENTS 5,514,694   5/1996   Powers ................................. 514/357

FOREIGN PATENT DOCUMENTS 195212   9/1986   European Pat. Off. .
363284   4/1990   European Pat. Off. .

OTHER PUBLICATIONS

Hu, Arch. Biochem. Biophys., 281, pp. 271–274 (received in PTO Sep. 10, 1990).

Burkhart, Tetrahedron Lett., 29, pp. 3433–3436 (1988).

*Primary Examiner*—Michael L. Shippen
*Attorney, Agent, or Firm*—Deveau, Colton & Marquis

[57] ABSTRACT

A novel class of peptide α-ketoamides useful for selectively inhibiting serine proteases, selectively inhibiting cysteine proteases, generally inhibiting all serine proteases, and generally inhibiting all cysteine proteases, having the formula $M_1$-AA-NH—$CHR_2$—CO—CO—$NR_3R_4$, $M_1$-$AA_2$-$AA_1$-CO—$NR_3R_4$, $M_1$-AA-AA-AA-CO—$NR_3R_4$, $M_1$-AA-AA-AA-AA-CO—$NR_3R_4$, or $M_1$-AA-CO—$NR_3R_4$.

5 Claims, No Drawings

PEPTIDES KETOAMIDES

This is a continuation of application Ser. No. 08/247,081 filed on May 20, 1994, now abandoned, which is a continuation of Ser. No. 08/118,997 filed on Sep. 9, 1993, now abandoned, which is a continuation of Ser. No. 07/815,073 filed on Dec. 27, 1991, now abandoned.

BACKGROUND OF THE INVENTION

1. Field of the Invention

This invention relates to a novel class of peptide ketoamides useful for selectively inhibiting serine proteases, selectively inhibiting cysteine proteases, generally inhibiting all serine proteases, and generally inhibiting all cysteine proteases. Serine proteases and cysteine proteases are involved in numerous disease states and inhibitors for these enzymes can be used therapeutically for the treatment of diseases involving serine proteases or cysteine proteases. We have discovered that peptide α-ketoamides can be constructed to inhibit selectively individual serine or cysteine proteases or groups of serine or cysteine proteases. We have found that peptide ketoamides which contain hydrophobic aromatic amino acid residues in the $P_1$ site are potent inhibitors of chymases and chymotrypsin-like enzymes. Ketoamides containing small hydrophobic amino acid residues at the $P_1$ position are good inhibitors of elastases. Inhibitors of elastases and chymases are useful as anti-inflammatory agents. We show that peptide ketoamides which contain cationic amino acid residues such as Arg and Lys in the $P_1$ site will be potent inhibitors of trypsin and blood coagulation enzymes. These inhibitors are thus useful as anticoagulants. Cysteine proteases such as papain, cathepsin B, and calpain I and II are also inhibited by ketoamides. Ketoamides with aromatic amino acid residues in the $P_1$ site are good inhibitors for cathepsin B and papain. Thus, they would have utility as anticancer agents. Ketoamides with either aromatic amino acid residues or small hydrophobic alkyl amino acid residues at $P_1$ are good inhibitors of calpain I and II. These inhibitors are useful as neuroprotectants and can be used as therapeutics for the treatment of neurodegeneration and stroke.

2. Nomenclature

In discussing the interactions of peptides with serine and cysteine proteases, we have utilized the nomenclature of Schechter and Berger [Biochem. Biophys. Res. Commun. 27, 157–162 (1967); incorporated herein by reference]. The individual amino acid residues of a substrate or inhibitor are designated $P_1$, $P_2$, etc. and the corresponding subsites of the enzyme are designated $S_1$, $S_2$, etc. The scissile bond of the substrate is $S_1$—$S_1'$. The primary substrate recognition site of serine proteases is $S_1$. The most important recognition subsites of cysteine proteases are $S_1$ and $S_2$.

Amino acid residues and blocking groups are designated using standard abbreviations [see J. Biol. Chem. 260, 14–42 (1985) for nomenclature rules; incorporated herein by reference]. An amino acid residue (AA) in a peptide or inhibitor structure refers to the part structure —NH—CHR$_1$—CO—, where R$_1$ is the side chain of the amino acid residue AA. A peptide α-ketoester residue would be designated -AA-CO—OR which represents the part structure —NH—CHR$_1$—CO—CO—OR. Thus, the ethyl ketoester derived from benzoyl alanine would be designated Bz-Ala-CO-OEt which represents C$_6$H$_5$CO—NH—CHMe—CO—CO—OEt. Peptide ketoamide residues would be designated -AA-CO—NH-R. Thus, the ethyl keto amide derived from Z-Leu-Phe-OH would be designated Z-Leu-Phe-CO—NH-Et which represents C$_6$H$_5$CH$_2$OCO—NH—CH(CH$_2$CH(CH$_2$)—CO—NH—CH(CH$_2$Ph)—CO—CO—NH—Et.

3. Description of the Related Art

Cysteine Proteases. Cysteine proteases such as calpain use a cysteine residue in their catalytic mechanism in contrast to serine proteases which utilize a serine residue. Cysteine proteases include papain, cathepsin B, calpains, and several viral enzymes. Neural tissues, including brain, are known to possess a large variety of proteases, including at least two calcium stimulated proteases termed calpains. Calpains are present in many tissues in addition to the brain. Calpain I is activated by micromolar concentrations of calcium while calpain II is activated by millimolar concentrations. In the brain, calpain II is the predominant form, but calpain I is found at synaptic endings and is thought to be the form involved in long term potentiation, synaptic plasticity, and cell death. Other Ca$^{2+}$ activated cysteine proteases may exist, and the term "calpain" is used to refer to all Ca$^{2+}$ activated cysteine proteases, including calpain I and calpain II. The terms "calpain I" and "calpain II" are used herein to refer to the micromolar and millimolar activated calpains, respectively, as described above. While calpains degrade a wide variety of protein substrates, cytoskeletal proteins seem to be particularly susceptible to attack. In some cases, the products of the proteolytic digestion of these proteins by calpain are distinctive and persistent over time. Since cytoskeletal proteins are major components of certain types of cells, this provides a simple method of detecting calpain activity in cells and tissues. Thus, calpain activation can be measured indirectly by assaying the proteolysis of the cytoskeletal protein spectrin, which produces a large, distinctive and biologically persistent breakdown product when attacked by calpain [Siman, Baudry, and Lynch, Proc. Natl. Acad. Sci. USA 81, 3572–3576 (1984); incorporated herein by reference]. Activation of calpains and/or accumulation of breakdown products of cytoskeletal elements has been observed in neural tissues of mammals exposed to a wide variety of neurodegenerative diseases and conditions. For example, these phenomena have been observed following ischemia in gerbils and rats, following stroke in humans, following administration of the toxins kainate, trimethyltin or colchicine in rats, and in human Alzheimer's disease.

Several inhibitors of calpain have been described including peptide aldehydes such as Ac-Leu-Leu-Nle-H and leupeptin (Ac-Leu-Leu-Arg-H), as well as epoxysuccinates such as E-64. These compounds are not especially useful at inhibiting calpain in neural tissue in vivo because they are poorly membrane permeant and, accordingly, are not likely to cross the blood brain barrier very well. Also, many of these inhibitors have poor specificity and will inhibit a wide variety of proteases in addition to calpain. Other classes of compounds which inhibit cysteine proteases include peptide diazomethyl ketone [Rich, D. H., in Protease Inhibitors, Barrett A. J., and Salversen, G., Eds., Elsevier, New York, 1986, pp 153–178; incorporated herein by reference). Peptide diazomethyl ketones are potentially carcinogenic and are thought to be poorly membrane permeant and to have low specificity. Thus, no effective therapy has yet been developed for most neurodegenerative diseases and conditions. Millions of individuals suffer from neurodegenerative diseases and thus, there is a need for therapies effective in treating and preventing these diseases and conditions.

Cathepsin B is involved in muscular dystrophy, myocardial tissue damage, tumor metastasis, and bone resorption. In addition, a number of viral processing enzymes, which are essential for viral infection, are cysteine proteases.

Inhibitors of cysteine proteases would have multiple therapeutic uses.

Serine Proteases. Serine proteases play critical roles in several physiological processes such as digestion, blood coagulation, complement activation, fibrinolysis, viral infection, fertilization, and reproduction. Serine proteases are not only a physiological necessity, but also a potential hazard if they are not controlled. Uncontrolled proteolysis by elastases may cause pancreatitis, emphysema, rheumatoid arthritis, bronchial inflammation and adult respiratory distress syndrome. It has been suggested that a new trypsin-like cellular enzyme (tryptase) is involved in the infection of human immunodeficiency virus type 1 [HIV-1; Hattori et al., FEBS Letters 248, pp. 48–52 (1989)], which is a causative agent of acquired immunodeficiency syndrome (AIDS). Plasmin is involved in tumor invasiveness, tissue remodeling, blistering, and clot dissociation. Accordingly, specific and selective inhibitors of these proteases should be potent anticoagulants, anti-inflammatory agents, anti-tumor agents and anti-viral agents useful in the treatment of protease-related diseases [Powers and Harper, Proteinase Inhibitors, pp 55–152, Barrett and Salvesen, eds., Elsevier, (1986); incorporated herein by reference]. In vitro proteolysis by chymotrypsin, trypsin or the elastase family is a serious problem in the production, purification, isolation, transport or storage of peptides and proteins.

Elastase inhibitors are anti-inflammatory agents which can be used to treat elastase-associated inflammation including rheumatoid arthritis and emphysema. Although the naturally occurring protease inhibitor, α1-protease inhibitor (α1-PI) has been used to treat patients with emphysema, this protein inhibitor is not widely used clinically due to the high dosage needed for treatment and the difficulty of producing large quantifies. Therefore, small molecular weight elastase inhibitors are needed for therapy. Other low molecular weight elastase inhibitors have utility for the treatment of emphysema and intimation (see: 1-carpapenem-3-carboxylic esters as anti-inflammatory agents, U.S. Pat. No. 4,493,839; N-carboxyl-thienamycin esters and analogs thereof as anti-inflammatory agents, U.S. Pat. No. 4,495,197; incorporated herein by reference).

Anticoagulants and antithrombotic drugs are used in a variety of thrombotic disorders. The 1990 Physician's Desk Reference lists several anticoagulant drugs (heparin, protamine sulfate and warfarin), a few antiplatelet drugs (aspirin) and several thrombolytic agents. Heparin and warfarin are commonly used clinically for prevention and treatment of venous thrombosis and pulmonary embolism. Heparin inhibits the blood coagulation activity by accelerating the binding of natural plasma protease inhibitor antithrombin III with coagulation factors, and warfarin acts as a vitamin K antagonist and inhibits the synthesis of coagulation factors. None of the anticoagulant drugs, antithrombotic drugs, fibrinolytic agents and antiplatelet drugs are highly effective in all clinical situations and many induce side reactions [Von Kaulla, Burger's Medicinal Chemistry, Part II, pp 1081–1132, Wolff, ed., (1979); incorporated herein by reference]. Coagulation disorders such as disseminated intravascular coagulation, bleeding complications of medical and surgical procedures and bleeding complications of systemic illness are still difficult to manage [Ingram, Brozovic and Slater, Bleeding Disorders, pp 1–413, Blackwell Scientific Publications, (1982); incorporated herein by reference]. In the treatment of patients with coagulation problems, anticoagulant or antithrombotic agents of diverse mechanisms are urgently sought in order to provide better medical care. Inhibitors for the trypsin-like enzymes involved in blood coagulation are useful anticoagulants in vivo [see for example: H-D-Phe-Pro-Arg-$CH_2C_1$, Hanson and Harker, Proc. Natl. Acad. Sci. 85, 3184–3188 (1988); 7-Amino-4-chloro-3-(3-isothiureidopropoxy)isocoumarin (ACITIC), Oweida, Ku, Luresden, Karo, and Powers, Thrombos. Res. 58, 191–197 (1990); incorporated herein by reference].

Ketoesters. A few amino acid and peptide ketoesters and ketoacids have been previously reported. Cornforth and Cornforth [J. Chem. Soc., 93–96 (1953); incorporated herein by reference] report the synthesis of the ketoacids $PhCH_2CO$-Gly-CO—OH and Ac-Gly-CO—OH upon hydrolysis of heterocyclic molecules. Charles et al. [J. Chem. Soc. Perkin I, 1139–1146 (1980); incorporated herein by reference] use ketoesters for the synthesis of bicyclic heterocycles. They report the synthesis of n-BuCO-Ala-CO-OEt, PrCO-Ala-CO-OEt, cyclopentylCO-Ala-CO-OEt, PrCO-PhGly-CO-OEt, and Bz-Ala-CO-OEt. Hori et al. [Peptides: Structure and Function-Proceedings of the Ninth American Peptide Symposium (Deber, Hruby, and Kopple, Eds.) Pierce Chemical Co., pp 819–822 (1985); incorporated herein by reference] report Bz-Ala-CO-OEt, Bz-Ala-CO—OH, Z-Ala-Ala-Abu-CO-OEt, Z-Ala-Ala-Abu-CO-OBzl, and Z-Ala-Ala-Ala-Ala-CO-OEt (Abu=2-aminobulanoic acid or aminobutyric acid) and report that these compounds inhibit elastase. Trainer [Trends Pharm. Sci. 8, 303–307 (1987); incorporated herein by reference] comments on one of this compounds. Burkhart, J., Peet, N. P., and Bey, P. [Tetrahedron Lett. 29, 3433–3436 (1988); incorporated herein by reference] report the synthesis of Z-Val-Phe-CO-OMe and Bz-Phe-CO-OMe.

Mehdi et al., [Biochem. Biophys. Res. Comm. 166, 595–600 (1990); incorporated herein by reference] report the inhibition of human neutrophil elastase and cathepsin G by peptide α-ketoesters. Angelastro et al., [J. Med. Chem. 33, 13–16 (1990); incorporated herein by reference] report some α-ketoesters which are inhibitors of calpain and chymotrypsin. Hu and Abeles [Arch. Biochem. Biophys. 281, 271–274 (1990)]; incorporated herein by reference] report some peptidyl α-ketoamides and α-ketoacids which are inhibitors of cathepsin B and papain. Peet et al. [J. Med. Chem. 33, 394–407 (1990); incorporated herein by reference] report some peptidyl α-ketoesters which are inhibitors of porcine pancreatic elastase, human neutrophil elastase, and rat & human neutrophil cathepsin G.

Ketoamides. A single peptide ketoamide is reported in the literature by Hu and Abeles [Arch. Biochem. Biophys. 281, 271–274 (1990)]. This compound Z-Phe-$NHCH_2CO$—CO—NH-Et or Z-Phe-Gly-CO—NH-Et is reported to be an inhibitor of papain ($K_I$=1.5 μM) and cathepsin B ($K_I$=4 μM).

SUMMARY OF THE INVENTION

We have discovered that peptide and amino acid α-ketoamide derivatives are a novel group of inhibitors for serine proteases and cysteine proteases. Inhibitors are compounds that reduce or eliminate the catalytic activity of the enzyme. We have discovered that peptide α-ketoamide derivatives, which have an amino acid sequence similar to that of good substrates for a particular protease, are good inhibitors for that protease. Thus, we are able to predict the structures of new inhibitors for other serine and cysteine proteases based on knowledge of their substrate specificities.

We have discovered some peptide α-ketoamide derivatives which are specific inhibitors for chymotrypsin. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. Inhibitors with these residues at $P_1$ are good chymotrypsin and chymase inhibitors. Trypsin and trypsin-like enzymes normally cleave peptide bonds in proteins and peptides where the amino acid residue on the carbonyl side of the split bond ($P_1$ residue) is Lys or Arg. We show that peptide α-ketoamide derivatives which have Lys or Arg at $P_1$ will be good inhibitors for these enzymes. Elastase and elastase-like enzymes cleave peptide bonds where the $P_1$ amino acid is Ala, Val, Ser, Leu and other similar amino acids. We shown that inhibitors with these residues at $P_1$ are good elastase inhibitors. All of the above enzymes have extensive secondary specificity and recognize amino acid residues removed from the $P_1$ residue.

The peptide α-ketoamide derivatives are also novel and potent inhibitors of cysteine proteases including calpains and cathepsin B. The calpain inhibitors are useful for treatment of various neurodegenerative diseases and conditions, including ischemia, stroke, and Alzheimer's disease.

The new protease inhibitors, especially the elastase inhibitors, trypsin inhibitors, and chymase inhibitors are useful for controlling tissue damage and various inflammatory conditions mediated by proteases such as blistering. The inhibitors for blood coagulation enzymes will be useful anticoagulants and could be used to treat thrombosis.

The peptide and amino acid α-ketoamide derivatives are also useful in vitro for inhibiting trypsin, elastase, chymotrypsin and other serine proteases of similar specificity, and for inhibiting serine proteases in general. The inhibitors can be used to identify new proteolytic enzymes encountered in research. They can also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons. For some uses a specific inhibitor would be desirable, while in other cases, an inhibitor with general specificity would be preferred.

DETAILED DESCRIPTION OF THE INVENTION

Peptide α-ketoamides are transition state analog inhibitors for serine proteases and cysteine proteases. Peptide α-ketoamides containing hydrophobic amino acid residues in the $P_1$ site have been found to be excellent inhibitors of serine proteases including porcine pancreatic elastase and bovine chymotrypsin. We show that peptide α-ketoamides containing amino acid residues with cationic side chains in the $P_1$ site will be excellent inhibitors of several serine proteases including bovine trypsin, bovine thrombin, human plasma kallikrein, porcine pancreatic kallikrein, human factor XIa and human plasmin. Peptide α-ketoamides containing amino acid residues with hydrophobic side chain at the $P_1$ site have also been found to be excellent inhibitors of several cysteine proteases including papain, cathepsin B, calpain I, and calpain II. These structures may be used in vivo to treat diseases such as emphysema, adult respiratory distress syndrome, rheumatoid arthritis and pancreatitis which result from uncontrolled proteolysis by elastase, chymotrypsin, trypsin and related serine proteases. These inhibitors may be used in vitro to prevent proteolysis which occurs in the process of production, isolation, purification, storage or transport of peptides and proteins. These inhibitors may be useful as therapeutic agents for treatment of neurodegeneration, viral infections, muscular dystrophy, myocardial tissue damage, tumor metastasis, and bone resorption.

The novel class of dipeptide α-ketoamides have the following structural formula:

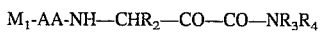

$M_1$—AA—NH—CHR$_2$—CO—CO—NR$_3$R$_4$ or a pharmaceutically acceptable salt, wherein $M_1$ represents H, $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2$H, amino, $C_{1-10}$ alkylamino, $C_{2-12}$ dialkylamino, $C_1C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH(CH$_2$CHEt$_2$)—COOH, alpha-aminoheptanoic acid, $NH_2$—CH(CH$_2$-1-napthyl)-COOH, $NH_2$—CH(CH$_2$-2-napthyl)-COOH, $NH_2$—CH(CH$_2$-cyclohexyl)-COOH, $NH_2$—CH(CH$_2$-cyclopentyl)-COOH, $NH_2$—CH(CH$_2$-cyclobutyl)-COOH, $NH_2$—CH(CH$_2$-cyclopropyl)-COOH, trifluoroleucine, and hexafluoroleucine;

$R_2$ is selected from the group consisting of $C_{1-8}$ branched and unbranched alkyl, $C_{1-8}$ branched and unbranched cyclized alkyl, and $C_{1-8}$ branched and unbranched fluoroalkyl;

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine [—N(CH$_2$CH$_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —CH$_2$CH$_2$OCH$_2$CH$_2$OH, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—CH$_2$CH$_2$-(4-hydroxyphenyl), and —NH—CH$_2$CH$_2$-(3-indolyl).

The novel class of dipeptide α-ketoamides also have the following structural formula:

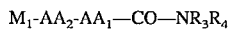

or a pharmaceutically acceptable salt, wherein $M_1$ represents H, NH$_2$—CO—, NH$_2$—CS—, NH$_2$—SO$_2$—, X—NH—CO—, X$_2$N—CO—, X—NH—CS—, X$_2$N—CS—, X—NH—SO$_2$, X$_2$N—SO$_2$—, X—CO—, X—CS—, X—SO$_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with in attached phenoxy group, and $C_{1-10}$ alkyl with an attached phenoxy group substituted with K on the phenoxy group;

J is selected from the group consisting of halogen, COOH, OH, CN, NO$_2$, NO$_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, NO$_2$, CN, OH, CO$_2$H, amino, $C_{1-10}$ alkylamino, $C_{2-12}$ dialkylamino, $C_1$-$C_{10}$ acyl, and $C_{1-10}$ alkoxy-CO—, and $C_{1-10}$ alkyl-S—;

$AA_1$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CH$_2$)—COOH, alpha-aminoheptanoic acid, NH$_2$—CH(CH$_2$-1-napthyl)-COOH, NH$_2$—CH(CH$_2$-2-napthyl)-COOH, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, trifluoroleucine, and hexafluoroleucine;

$AA_2$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-1-napthyl)-COOH, NH$_2$—CH(CH$_2$-2-napthyl)-COOH, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, trifluoroleucine, and hexafluoroleucine;

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine [—N(CH$_2$CH$_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —CH$_2$CH$_2$OCH$_2$CH$_2$OH, $C_{1-10}$ with a attached 4-pyridyl group, $C_{1-10}$ with an attached 3-pyridyl group, $C_{1-10}$ with an attached 2-pyridyl group, $C_{1-10}$ with an attached cyclohexyl group, —NH—CH$_2$CH$_2$-(4-hydroxyphenyl), and —NH—CH$_2$CH$_2$-(3-indolyl).

The novel class of tripeptide α-ketoamides have the following structural formula:

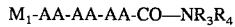

or a pharmaceutically acceptable salt, wherein $M_1$ represents H, NH$_2$—CO—, NH$_2$—CS—, NH$_2$—SO$_2$—, X—NH—CO—, X$_2$N—CO—, X—NH—CS—, X$_2$N—CS—, X—NH—SO$_2$, X$_2$N—SO$_2$—, X—CO—, X—CS—, X—SO$_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, NO$_2$, NH$_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group Consisting of halogen, $C_{1-10}$ alkyl, $C_{1-10}$ perfluoroalkyl, $C_{1-10}$ alkoxy, NO$_2$, CN, OH, CO$_2$H, amino, $C_{1-10}$ alkylamino, $C_{2-12}$ dialkylamino, $C_1$-$C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-1-napthyl)-COOH, $NH_2$—$CH(CH_2$-2-napthyl)-COOH, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, trifluoroleucine, and hexafluoroleucine;

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine [—$N(CH_2CH_2)O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), and —NH—$CH_2CH_2$-(3-indolyl).

The novel class of tetrapeptide α-ketoamides have the following structural formula:

$M_1$-AA-AA-AA-AA-CO—$NR_3R_4$ or a pharmaceutically acceptable salt, wherein $M_1$ represents H, $NH_2$—CO—, $NH_2$—CS—, $NH_2$—$SO_2$, X—NH—CO—, $X_2N$—CO—, X—NH—CS—, $X_2N$—CS—, X—NH—$SO_2$—, $X_2N$—$SO_2$—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-1-napthyl)-COOH, $NH_2$—$CH(CH_2$-2-napthyl)-COOH, $NH_2$—$CH(CH_2$-cyclohexyl)-COOH, $NH_2$—$CH(CH_2$-cyclopentyl)-COOH, $NH_2$—$CH(CH_2$-cyclobutyl)-COOH, $NH_2$—$CH(CH_2$-cyclopropyl)-COOH, trifluoroleucine, and hexafluoroleucine;

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine [—$N(CH_2CH_2)O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), and —NH—$CH_2CH_2$-(3-indolyl).

The novel class of amino acid α-ketoamides have the following structural formula:

$M_1$-AA-CO—$NR_3R_4$ or a pharmaceutically acceptable salt, wherein $M_1$ represents H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$-$C_{10}$ acyl, and $C_{1-10}$ alkoxy-CO—, and $C_{1-10}$ alkyl-S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2-CH(CH_2CHEt_2)-COOH$, alpha-aminoheptanoic acid, $NH_2-CH(CH_2\text{-}1\text{-napthyl})\text{-}COOH$, $NH_2-CH(CH_2\text{-}2\text{-napthyl})\text{-}COOH$, $NH_2-CH(CH_2\text{-cyclohexyl})\text{-}COOH$, $NH_2-CH(CH_2\text{-cyclopentyl})\text{-}COOH$, $NH_2-CH(CH_2\text{-cyclobutyl})\text{-}COOH$, $NH_2-CH(CH_2\text{-cyclopropyl})\text{-}COOH$, trifluoroleucine, and hexafluoroleucine;

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine $[-N(CH_2CH_2)O]$ ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, $-CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, $-NH-CH_2CH_2\text{-}(4\text{-hydroxyphenyl})$, and $-NH-CH_2CH_2\text{-}(3\text{-indolyl})$.

The following compounds are representatives of the invention:
Z-Leu-Phe-CONH-Et
Z-Leu-Phe-CONH-nPr
Z-Leu-Phe-CONH-nBu
Z-Leu-Phe-CONH-iBu
Z-Leu-Phe-CONH-Bzl
Z-Leu-Phe-CONH—$(CH_2)_2$Ph
Z-Leu-Abu-CONH-Et
Z-Leu-Abu-CONH-nPr
Z-Leu-Abu-CONH-nBu
Z-Leu-Abu-CONH-iBu
Z-Leu-Abu-CONH-Bzl
Z-Leu-Abu-CONH—$(CH_2)_2$Ph
Z-Leu-Abu-CONH—$(CH_2)_3$—$N(CH_2CH_2)_2O$
Z-Leu-Abu-CONH—$(CH_2)_7CH_3$
Z-Leu-Abu-CONH—$(CH_2)_2$OH
Z-Leu-Abu-CONH—$(CH_2)_2O(CH_2)_2OH$
Z-Leu-Abu-CONH—$(CH_2)_{17}CH_3$
Z-Leu-Abu-CONH—$CH_2$—$C_6H_3(OCH_3)_2$
Z-Leu-Abu-CONH—$CH_2$—$C_4H_4N$ Materials and Methods. HEPES, heparin, and A23187 were obtained from Calbiochem. Suc-Leu-Tyr-AMC and chromogenic substrates were obtained from Sigma. Calpain I was purified from human erythrocytes according to the method of Kitahara (Kitahara et al., J. Biochem. 95, 1759–1766) omitting the Blue-Sepharose step. Calpain II from rabbit muscle and cathepsin B were purchased from Sigma. Papain was purchased from Calbiochem.

Assay of Inhibitory Potency. Peptide α-ketoamides were assayed as reversible enzyme inhibitors. Various concentrations of inhibitors in Me$_2$SO were added to the assay mixture which contained buffer and substrate. The reaction was started by the addition of the enzyme and the hydrolysis rates were followed spectrophotometrically or fluorimetrically.

Calpain I from human erythrocytes and calpain II from rabbit were assayed using Suc-Leu-Tyr-AMC [Sasaki et al., J. Biol. Chem. 259, 12489–12494 (1984); incorporated herein by reference], and the AMC (7-amino-4-methylcoumarin) release was followed fluorimetrically (excitation at 380 nm, and emmision at 460 nm). Calpains were assayed in 25 mM Tris pH=8.0, 10 mM CaCl$_2$. Fluorescence was followed using a Gilson FL-1A fluorometer or a Perkin-Elmer 203 Fluorescence spectrometer. Cathepsin B was assayed in 20 mM sodium acetate pH=5.2, 0.5 mM dithiothreitol using Bz-Phe-Val-Arg-p-nitroanilide as substrate. Alternately, cathepsin B was assayed with Z-Arg-Arg-AFC [Barrett and Kirschke, Methods Enzymol. 80, 535–561 (1981); incorporated herein by reference], and the AFC (7-amino-4-trifluoromethylcoumarin) release was followed fluorimetrically (excitation at 400 nm and emmision at 505 nm). Papain was assayed in 100 mM KPO$_4$, 1 mM EDTA, 2.5 mM cysteine pH=6.0 using Bz-Arg-AMC or Bz-Arg-NA [Kanaoka et al., Chem. Plmrm. Bull. 25, 3126–3128 (1977); incorporated herein by reference] as a substrate. The AMC (7-amino-4-methylcoumarin) release was followed fluorimetrically (excitation at 380 nm, and emmision at 460 nm). Enzymatic hydrolysis rates were measured at various substrate and inhibitor concentrations, and $K_I$ values were determined by either Lineweaver-Burk plots or Dixon plots.

A 0.1M Hepes, 0.5M NaCl, pH 7.5 buffer was utilized for human leukocyte elastase (HLE), porcine pancreatic elastase (PPE), chymotrypsin and cathepsin G. A 0.1 Hepes, 0.01M CaCl$_2$, pH 7.5 buffer was utilized for trypsin, plasmin, and coagulation enzymes. A 50 mM Tris-HCl, 2 mM EDTA, 5 mM cysteine, pH 7.5 was used as a buffer for papain. A 88 mM KH$_2$PO$_4$, 12 mM Na$_2$HPO$_4$, 1.33 mM EDTA, 2.7 mM cysteine, pH 6.0 solution was used as a buffer for cathepsin B. A 20 mM Hepes, 10 mM CaCl$_2$, 10 mM mercatoethanol, pH 7.2 buffer was utilized for calpain I and calpain II.

HLE and PPE were assayed with MeO-Suc-Ala-Ala-Pro-Val-NA and Suc-Ala-Ala-Ala-NA, respectively [Nakajima et al., J. Biol. Chem. 254, 4027–4032 (1979); incorporated herein by reference]. Human leukocyte cathepsin G and chymotrypsin A$_\alpha$ were assayed with Suc-Val-Pro-Phe-NA [Tanaka et al., Biochemistry 24, 2040–2047 (1985); incorporated herein by reference]. The hydrolysis of peptide 4-nitroanilides was measured at 410 nm [$\epsilon_{410}$=8800 M$^{-1}$cm$^{-1}$; Erlanger et al., Arch. Biochem. Biophys. 95, pp 271–278 (1961); incorporated herein by reference]. Trypsin, thrombin, human plasma kallikrein, porcine pancreatic kallikrein, human factor XIa, and human plasmin were assayed with Z-Arg-SBzl or Z-Gly-Arg-SBu-i [McRae et al., Biochemistry 20, 7196–7206 (1981); incorporated herein by reference]. All peptide thioester hydrolysis rates were measured with assay mixtures containing 4,4'-dithiodipyridine [$\epsilon_{324}$=19800 M$^{-1}$cm$^{-1}$; Grasetti & Murray, Arch. Biochem. Biophys. 119, 41–49 (1967); incorporated herein by reference].

Platelet membrane permeability assay. Calpain-mediated breakdown of spectrin was measured by quantitative densitometry of the calpain-specific 150/155 kDa spectrin fragment doublet [see Siman et al., Proc. Natl. Acad. Sci. USA 81, 3572–3576 (1984)]. Platelets were isolated by a modification of the method of Ferrell and Martin [J. Biol. Chem. 264, 20723–20729 (1989)]. Blood (15–20 ml) was drawn from male Sprague-Dawley rats into 1/10th volume of 100 mM EDTA-citrate, and centrifuged 10 minutes at 2000 rpm in a clinical centrifuge at room temperature. The plasma was resuspended in 15 ml of buffer 1 (136 mM NaCl, 2.7 mM KCl, 0.42 mM $NaH_2PO_4$, 12 mM $NaHCO_3$, 2 mM $MgCl_2$, 2 mg/ml BSA (Sigma), 5.6 mM glucose, 22 mM $Na_3$citrate pH 6.5) and platelets were isolated at 2200 rpm at room temperature for 10 minutes. Platelets were washed once in 15 ml buffer 1, then resuspended to $10^7$ cells/ml in buffer 2 (136 mM NaCl, 2.7 mM KCl, 0.42 mM $NaH_2PO_4$, 12 mM $NaHCO_3$, 2mM $MgCl$, 1 mg/ml BSA (Sigma), 5.6 mM glucose, 20 mM HEPES (Sigma) pH 7.4) and allowed to "rest" for a minimum of 10 minutes at room temperature before use.

Inhibitors were added from stock solutions made fresh in DMSO. 100 μl platelets, suspended to $10^7$ cells/ml in buffer 2, were incubated with 1 μl of an inhibitor solution for 5 minutes at room temperature prior to the addition of 2 mM $Ca^{2+}$ and 1 uM A23 187. After 10 minutes total exposure to inhibitor (5 minutes exposure to ionophore) at room temperature, platelets were reisolated at 14,000 rpm for 10 sec in a Beckman microfuge, dissolved in SDS-PAGE sample buffer, and heated to 90° C. for 3 minutes.

Samples were subjected to SDS-PAGE in 4–12% gradient mini gels (Novex) and transferred to nitrocellulose (Schleicher and Schuell 0.45 um) by electroblotting. Filters were blocked for 10 minutes in 0.25% gelatin, 1% BSA, 0.25% triton X100, 0.9% NaCl, 10 mM Tris-Cl pH 7.5, incubated overnight in the same solution containing antibody to rat spectrin, washed 3×10 minutes with 10 mM Tris-Cl pH 7.5, 0.5% triton X100, incubated 4 hours in wash buffer plus alkaline phosphatase conjugated goat anti-rabbit antibody (Biorad), and washed as above. Blots were developed using the Biorad AP conjugate substrate kit. Quantitative densitometry was used to obtain values for the intact spectrin bands and the 150/155 kDa breakdown product doublet.

Structure-Activity Relationships. Table I shows the inhibition constants ($K_I$) for cathepsin B, calpain I, and calpain II. Dipeptide α-ketoamides with Abu and Phe in the $P_1$ site and Leu in the $P_2$ site are potent inhibitors of calpain I and calpain I/. Z-Leu-Abu-CONH-Et is a better inhibitor of calpain I than Z-Leu-Phe-CONH-Et by 14 fold. Replacement of the Z group ($PhCH_2OCO$—) by similar groups such as $PhCH_2CH_2CO$—, $PhCH_2CH_2SO_2$—, $PhCH_2NHCO$—, and $PhCH_2NHCS$— would also result in good inhibitor structures. The best inhibitor of calpain II is Z-Leu-Abu-CONH—$(CH_2)_2$-Ph. Changing the $R_3$ and $R_4$ groups significantly improves the inhibitory potency toward calpain II. The best dipeptide inhibitors are those which have long alkyl side chains (e.g. Z-Leu-Abu-CONH—$(CH_2)_7CH_3$), alkyl side chains with phenyl substituted on the alkyl group (e.g. Z-Leu-Abu-CONH—$(CH_2)_2$-Ph, or alkyl groups with a morpholine ring substituted on the alkyl group [e.g. Z-Leu-Abu-CONH—$(CH_2)_3$)-Mpl, Mpl=—$N(CH_2CH_2)_2O$]. Dipeptide α-ketoamides with a small aliphatic amino acid residue or a Phe in the $P_1$ site are also good inhibitors for cathepsin B. The best inhibitor is Z-Leu-Abu-CONH-Et and replacement of the Z ($PhCH_2OCO$—) by $PhCH_2CH_2CO$—, $PhCH_2CH_2SO_2$—, $PhCH_2NHCO$—, and $PhCH_2NHCS$— would also result in good inhibitor structures.

TABLE 1

Inhibition of Cysteine Proteases by Peptide α-Ketoamides.

| Peptide α-Ketoamide | $K_I$ (μM) | | |
| --- | --- | --- | --- |
| | Calpain I | Calpain II | Cath B |
| Z—Leu—Abu—CONH—Et | 0.5 | 0.23 | 2.4 |
| Z—Leu—Abu—CONH—nPr | | 0.25 | 8 |
| Z—Leu—Abu—CONH—nBu | 0.2 | | 13 |
| Z—Leu—Abu—CONH—iBu | | 0.14 | 4 |
| Z—Leu—Abu—CONH—Bzl | | 0.35 | 2 |
| Z—Leu—Abu—CONH—$(CH_2)_2$—Ph | | 0.022 | |
| Z—Leu—Abu—CONH—$(CH_2)_3$—Mpl | | 0.041 | |
| Z—Leu—Abu—CONH—$(CH_2)_7CH_3$ | | 0.019 | |
| Z—Leu—Abu—CONH—$(CH_2)_{17}CH_3$ | | | |
| Z—Leu—Abu—CONH—$(CH_2)_2OH$ | | 0.078 | |
| Z—Leu—Abu—CONH—$(CH_2)_2O(CH_2)_2OH$ | 0.16 | | |
| Z—Leu—Phe—CONH—Et | 7.0 | 0.32 | 6 |
| Z—Leu—Phe—CONH—nPr | 15.0 | 0.05 | 3 |
| Z—Leu—Phe—CONH—nBu | | 0.028 | 3 |
| Z—Leu—Phe—CONH—iBu | | 0.065 | 4 |
| Z—Leu—Phe—CONH—Bzl | | 0.046 | |
| Z—Leu—Phe—CONH$(CH_2)_2$Ph | | 0.024 | |

Table II shows the inhibition constants ($K_I$) for PP elastase and chymotrypsin. Dipeptide α-ketoamides with Abu in the $P_1$ site are potent inhibitors of PP elastase. The structures with medium sized straight-chain alkyl groups such as n-Pr and n-Bu were better inhibitors than a small alkyl (Et) or a branched alkyl (i-Bu). Dipeptide α-ketoamides with Phe in the $P_1$ site are moderate inhibitors of chymotrypsin. The inhibitor with $R_3$=n-Bu and $R_4$=H was the best in the series. In general the inhibitors were more potent at inhibiting cysteine protease than serine proteases. Extending the peptide chain to tripeptide or tetrapeptide α-ketoamides would improve the inhibitory potency toward serine proteases.

TABLE II

Inhibition of Serine Proteases by Peptide α-Ketoamides.

| | $K_I$ (μM) | |
|---|---|---|
| Peptide α-Ketoamide | Chymo-trypsin | PP elastase |
| Z—Leu—Abu—CONH—Et | >150 | 65 |
| Z—Leu—Abu—CONH—nPr | >300 | 2 |
| Z—Leu—Abu—CONH—nBu | >300 | 5 |
| Z—Leu—Abu—CONH—iBu | >300 | 40 |
| Z—Leu—Abu—CONH—Bzl | >300 | |
| Z—Leu—Abu—CONH—(CH$_2$)$_2$—Ph | | |
| Z—Leu—Abu—CONH—(CH$_2$)$_3$—Mpl | | |
| Z—Leu—Abu—CONH—(CH$_2$)$_7$CH$_3$ | | |
| Z—Leu—Abu—CONH—(CH$_2$)$_{17}$CH$_3$ | | |
| Z—Leu—Abu—CONH—(CH$_2$)$_2$OH | | |
| Z—Leu—Abu—CONH—(CH$_2$)$_2$O(CH$_2$)$_2$OH | | |
| Z—Leu—Phe—CONH—Et | 73 | >150 |
| Z—Leu—Phe—CONH—nPr | 18 | >300 |
| Z—Leu—Phe—CONH—nBu | 8 | >100 |
| Z—Leu—Phe—CONH—iBu | 24 | |
| Z—Leu—Phe—CONH—Bzl | | |
| Z—Leu—Phe—CONH(CH$_2$)$_2$Ph | | |

Peptide α-ketoamide were substantially more stable in both plasma and liver than the corresponding peptide α-ketoesters (Table III). The peptide α-ketoamides were also much more effective in the platelet assay. Extending the R$_3$ group to an alkyl group or an alkyl group substituted with a phenyl group increased the membrane permeability of the inhibitors as indicated by increased potency in the platelet assay.

TABLE III

Half-lives in Plasma and in Liver and Activity in the Platelet Assay.

| Peptide α-Ketoamide or Ester | platelet | $t_{1/2}$ plasma | $t_{1/2}$ liver |
|---|---|---|---|
| Z—Leu—Abu—COOEt | 42 | 2.8 | |
| Z—Leu—Abu—COOn—Bu | 28 | | |
| Z—Leu—Abu—COOBzl | ++ | | |
| Z—Leu—Leu—Abu—COOEt | 40 | | |
| 2-NapSO2—Leu—Leu—Abu—COOEt | 100 | >60 | |
| 2-NapCO—Leu—Leu—Abu—COOEt | | 25 | |
| Tos—Leu—Leu—Abu—COOEt | 30 | 30 | |
| Z—Leu—Abu—COOH | 8 | >60 | >60 |
| Z—Leu—Abu—CONH—Et | 1.5 | >60 | >60 |

TABLE III-continued

Half-lives in Plasma and in Liver and Activity in the Platelet Assay.

| Peptide α-Ketoamide or Ester | platelet | $t_{1/2}$ plasma | $t_{1/2}$ liver |
|---|---|---|---|
| Z—Leu—Abu—CONH—nPr | 70 | >60 | >60 |
| Z—Leu—Abu—CONH—nBu | 2.0 | >60 | >60 |
| Z—Leu—Abu—CONH—iBu | 28 | >60 | |
| Z—Leu—Abu—CONH—Bzl | 1.5 | >60 | >60 |
| Z—Leu—Phe—COOEt | 42 | 7.8 | |
| Z—Leu—Phe—COOnBu | +++ | 7.7 | |
| Z—Leu—Phe—COOBz | ++ | 1.9 | |
| Z—Leu—Leu—Phe—COOEt | ++ | | |
| Z—Leu—Phe—COOH | 6.5 | >60 | >60 |
| Z—Leu—Phe—CONH—Et | 1.7 | >60 | >60 |
| Z—Leu—Phe—CONH—nPr | 24 | >60 | >60 |
| Z—Leu—Phe—CONH—nBu | 38 | >60 | >60 |
| Z—Leu—Phe—CONH—iBu | 22 | >60 | |
| Z—Leu—Phe—CONH—Bzl | | | |
| Z—Leu—Phe—CONH(CH$_2$)$_2$Ph | 3.0 | >60 | |
| Z—Leu—Nle—COOEt | 20 | 3.7 | |
| Z—Leu—Nva—COOEt | 40 | 2.8 | |
| Z—Leu—Met—COOEt | + | 8 | |

(+++ = excellent activity;
++ = good activity,
+ = moderate activity; quantitative measurements not yet complete)

Inhibition Mechanism. A crystal structure of one α-ketoester bound into the active site of porcine pancreatic elastase has been completed and a schematic drawing of the interactions observed is shown below. The active site Ser-195 oxygen of the enzyme has added to the carbonyl group of the ketoester to form a tetrahedral intermediate which is stabilized by interactions with the oxyanion hole. This structure resembles the tetrahedral intermediate involved in peptide bond hydrolysis and proves that α-ketoesters are transition-state analogs. His-57 is hydrogen bonded to the carbonyl group of the ester functional group, the peptide backbone on a section of PPE's backbone hydrogen bonds to the inhibitor to form a β-sheet, and the benzyl ester is directed toward the S' subsites. The side chain of the P$_1$ amino acid residue is located in the S$_1$ pocket of the enzyme. Interactions with ketoamides would be similar except for that there would be the possibility of forming an additional hydrogen bond with the NH group of the ketoamide functional group if R$_3$ or R$_4$ was H. If R$_3$ and/or R$_4$ are longer substutuents, then they would make favorable interactions with the S' subsites of the enzyme.

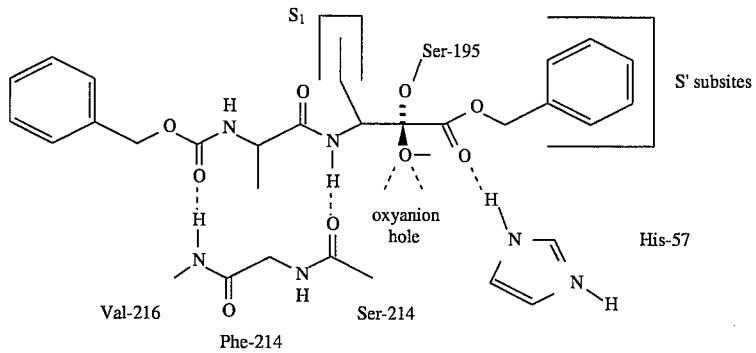

The active site of cysteine proteases share several features in common with serine proteases including an active site histidine residue. In place of the Ser-195, cysteine proteases have an active site cysteine residue which would add to the ketonic carbonyl group of the peptide keto acids, keto esters, or ketoamides to form an adduct very similar to the structure depicted above except with a cysteine residue replacing the serine- 195 residue. Additional interactions would occur between the extended substrate binding site of the cysteine protease and the inhibitor which would increase the binding affinity and specificity of the inhibitors.

Inhibitor Design and Selection. The peptide and amino acid α-ketoamide derivatives, as shown in the above crystal structure, bind to the enzymes using many of the interactions that are found in complexes of a particular individual enzyme with its substrates. In order to design an inhibitor for a particular serine or cysteine protease, it is necessary to: 1) find the amino acid sequences of good peptide substrates for that enzyme, and 2) place those or similar amino acid sequences into a α-ketoamide structure. Additional interactions with the enzyme can be obtained by tailoring the R group of the inhibitor to imitate the amino acid residues which are preferred by an individual protease at the $S_1'$ and $S_2'$ subsites. For example, ketoesters with $R_3$ and/or $R_4$=branched alkyl groups would interact effectively with serine and cysteine proteases which prefer Leu, Ile, and Val residues at $P_1'$ and/or $P_2'$, while amides with R=alkyl substituted with phenyl would interact effectively with serine and cysteine proteases which prefer Phe, Tyr, Trp residues at $P_1'$ and/or $P_2'$. Likewise, the $M_1$ group can be tailored to interact with the S subsites of the enzyme. This design strategy will also work when other classes of peptide inhibitors are used in place of the peptide substrate to gain information on the appropriate sequence to place in the ketoester, ketoacid, or ketoamide inhibitor. Thus, we are able to predict the structure of new inhibitors for other serine and cysteine proteases based on knowledge of their substrate specificities. Once a good inhibitor structure for a particular enzyme is found, it is then possible to change other characteristics such as solubility or hydrophobicity by adding substituents to the $M_1$ or $R_3$ and $R_4$ groups.

Elastase is an enzyme which hyrolyzes most effectively tetra- and tripeptides having $P_1$ residues with small alkyl side chains such as Ala and Val. MeO-Suc-Ala-Ala-Ala-Val-NA and Z-Ala-Ala-Ala-Ala-NA are good substrates (NA= 4-nitroanilide). Thus the corresponding α-ketoamide Z-Ala-Al a-Ala-DL-Ala-CO—$NR_3R_4$ and MeO-Suc-Ala-Ala-Pro-DL-Abu-CO—$NR_3R_4$ will be excellent elastase inhibitors. Suc-Phe-Leu-Phe-NA is an excellent substrate for chymotrypsin, cathepsin G, and mast cell chymases. Thus, the corresponding α-ketoamide will be an excellent inhibitor for these chymotrypsin-like enzymes. In the case of the cysteine protease calpain, a good inhibitor sequence is Ac-Leu-Leu-Nle-H. We have found that ketoesters related in structure such as Z-Leu-Abu-CO—$NR_3R_4$ and Z-Leu-Phe-CO—$NR_3R_4$ are potent inhibitors for calpain.

The following structures are predicted to be potent inhibitors for the listed enzymes. The inhibitor sequences were obtained from peptide substrate and/or inhibitor sequences in the protease literature.

| Structure | Enzyme |
|---|---|
| Z—Gly—Leu—Phe—CO—$NR_3R_4$ | for cathepsin G and RMCP II |
| MeO—Suc—Ala—Ala—Pro—Met—CO—$NR_3R_4$ | for cathepsin G |
| Boc—Ala—Ala—Asp—CO—$NR_3R_4$ | for human lymphocyte granzyme B |
| Suc—Pro—Leu—Phe—CO—$NR_3R_4$ and Boc—Ala—Ala—Phe—CO—$NR_3R_4$ | for RMCP I (RMCP = rat mast cell protease) |
| Boc—Gly—Leu—Phe—CO—$NR_3R_4$, Suc—Phe—Leu—Phe—CO—$NR_3R_4$ | for human and dog skin chymase |
| Boc—Ala—Ala—Glu—CO—$NR_3R_4$ | for S. aureus V-8 protease |
| Z—Gly—Gly—Pro—CO—$NR_3R_4$ | for human prolyl endopeptidase |
| Ala—Pro—CO—$NR_3R_4$ | for DPP IV |
| Suc—Ala—Ala—Pro—Val—CO—$NR_3R_4$ | for PPE |
| Suc—Lys(Cbz)—Val—Pro—Val—CO—$NR_3R_4$, adamantyl-$SO_2$—Lys(COCH$_2$CH$_2$CO$_2$H)—Ala—Val—CO—$NR_3R_4$, adamantyl-CH$_2$CH$_2$OCO—Glu(O-t-Bu—Pro—Val—CO—$NR_3R_4$, and adamantyl-$SO_2$—Lys(CO—$C_6H_4CO_2H$)—Ala—Val—CO—$NR_3R_4$ | for human leukocyte (neutrophil) elastase |
| Suc—Ala—Ala—Pro—Leu—CO—$NR_3R_4$ | for elastolytic proteinase from "Schistosoma mansoni" |
| Glu—Phe—Lys—CO—$NR_3R_4$ and Dns—Ala—Phe—Lys—CO—$NR_3R_4$ | for plasmin |
| D—Val—Gly—Arg—CO—$NR_3R_4$ and Dns—Glu—Gly—Arg—CO—$NR_3R_4$ | for factor Xa |
| Z—Phe—Arg—CO—$NR_3R_4$ and Z—Trp—Arg—CO—$NR_3R_4$ | for porcine pancreatic and human plasma kallikreins |
| Z—Lys—Arg—CO—$NR_3R_4$ | for human skin tryptase |
| Z—Gly—Arg—CO—$NR_3R_4$ | for human lung tryptase |
| Z—Ile—Ala—Gly—Arg—CO—$NR_3R_4$ | for factors IXa, Xa, XIa, XIIa and bovine plasma kallikrein |
| Glu—Gly—Arg—CO—$NR_3R_4$ | for urokinase |
| Dns—Phe—Pro—Arg—CO—$NR_3R_4$ | for plasminogen activator |
| Dns—Ile—Pro—Arg—CO—$NR_3R_4$ | for activated protein C |
| Z—Trp—Arg—CO—$NR_3R_4$ | for bovine factor IXa |
| Z—Gly—Arg—CO—$NR_3R_4$ | for bovine factor Xa and XIa |
| Z—Phe—Arg—CO—$NR_3R_4$ | for bovine factor XIIa |
| Dns—Glu—Gly—Arg—CO—$NR_3R_4$ | for human factor Xa |
| D—Phe—Pro—Arg—CO—$NR_3R_4$, D—MePhe—Pro—Arg—CO—$NR_3R_4$, and Boc—D—Phe—Pro—Arg—CO—$NR_3R_4$ | for human thrombin |
| Z—Phe—Gly—Arg—CO—$NR_3R_4$ | for trypsin |
| Cl—$C_6H_4CH_2$OCO—Phe—Gly—CO—$NR_3R_4$ | for papain |
| $C_6H_5CH_2$NHCO—Gly—Phe—Gly—CO—$NR_3R_4$ | for cathepsin B |

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine [—$N(CH_2CH_2)O$] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), and —NH—$CH_2CH_2$-(3-indolyl).

In Vitro Uses. To use the above inhibitors in vitro, they are dissolved in an organic solvent such as dimethylsulfoxide or ethanol, and are added to an aqueous solution containing serine and/or cysteine proteases. The final concentration of the organic solvent should be less than 25%. The inhibitors may also be added as solids or in suspension. The serine and cysteine protease inhibitors of this invention would be useful in a variety of experimental procedures where proteolysis is a significant problem. Inclusion of these inhibitors in a radioimmunoassay experiments would result in higher sensitivity. The use of these inhibitors in plasma fractionation procedures would result in higher fields of valuable plasma proteins and would make purification of the proteins easier. The inhibitors disclosed here could be used in cloning experiments utilizing bacterial cultures, yeast and human cells to yield a purified cloned product in higher yield.

The novel compounds of this invention are effective in the prevention of unnecessary proteolysis caused by chymotrypsin-like and elastase-like enzymes in the process of purification, transport and storage of peptides and proteins as shown in Table II by effective inhibition of chymotrypsin and elastase and other cysteine proteases.

In Vivo Uses. Effective inhibitors of the proteolytic function of human leukocyte elastase and chymotrypsin-like enzymes (Table II) would have anti-inflammatory activity and can be used to treat and control emphysema, adult respiratory distress syndrome and rheumatoid arthritis. Effective inhibitors of the proteolytic function of chymotrypsin and pancreatic elastase (Table II) are effective for theraputic use in the treatment of pancreatitis.

Peptide α-ketoamide can be used to control protein turnover, muscular dystrophy, myocardial tissue damage, tumor metastasis, and bone resorption as shown in Table I by effective inhibition of lysosomal cathepsin B in buffer. Peptide α-ketoamides can also be used as neuroprotectants or for the treatment of ischemia, stroke or Alzheimer's disease as shown in Table I by effective inhibiton of calpain I and calpain II.

Considerable evidence has shown that leukocyte elastase and/or related enzymes play a role in tumor cell metastasis [Salo et al., Int. J. Cancer 30, pp 669–673 (1973); Kao et al., Biochem. Biophys. Res. Comm. 105, pp 383–389 (1982); Powers, J. C. in Modification of Proteins, R. E. Feeney and J. R. Whitaker, eds., Adv. Chem. Ser 198, Amer. Chem. Soc., Wash., D.C. pp 347–367 (1982); all incorporated herein by reference], therefore it is suggested that compounds of this invention may have anti-tumor activity.

Pulmonary emphysema is a disease characterized by progressive loss of lung elasticity due to the destruction of lung elastin and alveoli. The destructive changes of lung parentchyma associated with pulmonary emphysema are caused by uncontrolled proteolysis in lung tissues [Janoff, Chest 83, 54–58 (1983); incorporated herein by reference]. A number of proteases have been shown to induce emphysema in animals [Marco et al., Am. Rev. Respir. Dis. 104, 595–598 (1971); Kaplan, J. Lab. Clin. Med. 82, 349–356 (1973); incorporated herein by reference], particularly human leukocyte elastase [Janoff, ibid 115, 461–478 (1977); incorporated herein by reference]. Leukocyte elastase and other mediators of inflammation also appear to play a role in diseases such as mucocutaneous lymph node syndrome [Reiger et al., Eur. J. Pediatr. 140, 92–97 (1983); incorporated herein by reference] and adult respiratory distress syndrome [Stockley, Clinical Science 64, 119–126 (1983); Lee et al., N. Eng. J. Med. 304, 192–196 (1981); Rinaldo, ibid 301, 900–909 (1982); incorporated herein by reference].

It is known that in vitro activity of elastase inhibitors correlates with in vivo activity in animal models of emphysema and inflammation [Otterness et al., editors, Advances in Intimation Research, Vol. 11, Raven Press 1986; incorporated herein by reference]. Prophylactic administration of an inhibitor of elastase significantly diminishes the extent of elastase-induced emphysema [Kleinerman et al., Am. Rev. Resir. Dis. 121, 381–387 (1980); Lucey et al., Eur. Respir. J. 2, 421–427 (1989); incorporated herein by reference]. Thus the novel inhibitors described here should be useful for the treatment of emphysema and inflammation. Elastase inhibitors have been used orally, by injection, or by instillation in the lungs in animal studies (Powers, Am. Rev. Respir. Dis., 127, s54–s58 (1983); Powers and Bengali, Am. Rev. Respir. Dis. 134, 1097–1100 (1986); these two articles are incorporated herein by reference). The inhibitors described above can be used by any of these routes.

Drug Delivery. For therapeutic use, the peptide α-ketoamides may be administered orally, topically or parenterally. The term parenteral as used includes subcutaneous injection, intravenous, intramuscular, intrasternal injection or infusion techniques. The dosage depends primarily on the specific formulation and on the object of the therapy or prophylaxis. The mount of the individual doses as well as the administration is best determined by individually assessing the particular case.

The pharmaceutical compositions containing the active ingredient may be in a form suitable for oral use, for example as tablets, troches, lozenges, aqueous or oily suspensions, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the peptide α-ketoamides or their pharmaceutically acceptable salts will normally be in the dosage range from 0.2 to 140 mg/kg of body weight. Administration is made by intravenous, intramuscular or subcutaneous injection. Accordingly, pharmaceutical compositions for parenteral administration will contain in a single dosage form about 10 mg to 7 gms of the compounds per dose. In addition to the active ingredient, these pharmaceutical compositions will usually contain a buffer, e.g. a phosphate buffer which keeps the pH in the range from 3.5 to 7 and also sodium chloride, mannitol or sorbitol for adjusting the isotonic pressure.

A composition for topical application can be formulated as an aqueous solution, lotion, jelly or an oily solution or suspension. A composition in the form of an aqueous solution is obtained by dissolving the compounds of this invention in aqueous buffer solution of pH 4 to 6.5 and if desired, adding a polymeric binder. An oily formulation for topical application is obtained by suspending the compounds of this invention in an oil, optionally with the addition of a swelling agent such as aluminum stearate and/or a surfactant.

SYNTHETIC METHODS

The α-ketoamide inhibitors are prepared from the corresponding α-ketoamide. The ketoester inhibitors are prepared by a two step Dakin-West from the corresponding peptide acid (Charles et al., J. Chem. Soc. Perkin 1, 1139–1146, 1980). This procedure can be utilized with either amino acid derivatives, dipeptide derivatives, tripeptide derivatives, or tetrapeptide derivatives as shown in the following scheme.

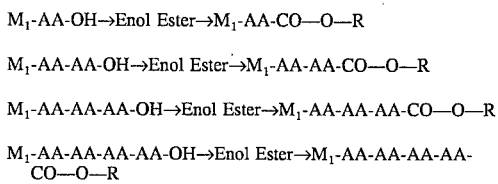

The precursor peptide can be prepared using standard peptide chemistry which is well described in publications such as The Peptides, Analysis, Synthesis, Biology, Vol. 1–9, published in 1979–1987 by Academic Press and Houben-Weyl Methoden der Organischen Chemie, Vol. 15, Parts 1 and 2, Synthese von Peptiden, published by Georg Thieme Verlag, Stuttgart in 1974 (both references incorporated herein by reference).

The $M_1$ group can be introduced using a number of different reaction schemes. First it could be introduced directly on an amino acid as shown in the following scheme (top), or the $M_1$ group could be introduced by reaction with an amino acid ester, followed by removal of the ester group to give the same product (bottom).

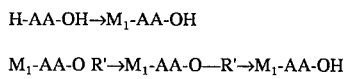

The techniques for introduction of the $M_1$ group is well documented in the The Peptides, Houben-Weyel, and many other textbooks on organic synthesis. For example reaction with cyanate or p-nitrophenyl cyanate would introduce a carbamyl group ($M_1=NH_2CO-$). Reaction with $Me_2NCOCl$ would introduce the $Me_2NCO-$ group. Reaction with p-nitrophenyl thiocarbamate would introduce a thio carbamyl group ($M_1=NH_2CS-$). Reaction with $NH_2SO_2Cl$ would introduce the $NH_2SO_2-$ group. Reaction with $Me_2NSO_2Cl$ would introduce the $Me_2NSO_2-$ group. Reaction with a substituted alkyl or aryl isocyanate would introduce the X—NH—CO— group where X is a substituted alkyl or aryl group. Reaction with a substituted alkyl or aryl isothiocyanate would introduce the X—NH—CS— group where X is a substututed alkyl or aryl group. Reaction with $X-SO_2-Cl$ would introduce the $X-SO_2-$ group. Reaction with a substituted alkyl or aryl acid chloride would introduce an acyl group (M=X—CO—). For example, reaction with $MeO-CO-CH_2CH_2-CO-Cl$ would give the X—CO— group where X is a $C_2$ alkyl substituted with a $C_1$ alkyl-OCO— group. Reaction with a substituted alkyl or aryl thioacid chloride would introduce a thioacyl group (M=X—CS—). Reaction with an a substituted alkyl or aryl sulfonyl chloride would introduce an $X-SO_2-$ group. For example reaction with dansyl chloride would give the $X-SO_2-$ derivative where X was a naphthyl group mono substituted with a dimethylamino group. Reaction with a substituted alkyl or aryl chloroformate would introduce a X—O—CO— group. Reaction with a substituted alkyl or aryl chlorothioformate would introduce a X—O—CS—. There are many alternate reaction schemes which could be used to introduce all of the above $M_1$ groups to give either $M_1$-AA-OH or $M_1$-AA-OR'.

The $M_1$-AA-OH derivatives could then be used directly in the Dakin-West reaction or could be converted into the dipeptides, tripeptides, and tetrapeptides $M_1$-AA-AA-OH, $M_1$-AA-AA-AA-OH, or $M_1$-AA-AA-AA-AA-OH which could be be used in the Dakin-West reaction. The substituted peptides $M_1$-AA-AA-OH, $M_1$-AA-AA-AA-OH, or $M_1$-AA-AA-AA-AA-OH could also be prepared directly from H-AA-AA-OH, H-AA-AA-AA-OH, or H-AA-AA-AA-AA-OH using the reactions described above for introduction of the $M_1$ group. Alternately, the $M_1$ group could be introduced by reaction with carboxyl blocked peptides to give $M_1$-AA-AA-OR', $M_1$-AA-AA-AA-OR', or $M_1$-AA-AA-AA-AA-OR', followed by the removal of the blocking group R'.

The R group in the ketoester structures is introduced during the Dakin-West reaction by reaction with an oxalyl chloride Cl—CO—CO—O—R. For example, reaction of $M_1$-AA-AA-OH with ethyl oxalyl chloride Cl—CO—CO—O-Et gives the keto ester $M_1$-AA-AA-CO—O-Et. Reaction of $M_1$-AA-AA-AA-OH with Cl—CO—CO—O—Bzl would give the ketoester $M_1$-AA-AA-AA-CO—O-Bzl. Clearly a wide variety of R groups can be introduced into the ketoester structure by reaction with various alkyl or arylalkyl oxalyl chlorides ($C_1$—CO—CO—O—R). The oxalyl chlorides are easily prepared by reaction of an alkyl or arylalkyl alcohol with oxalyl chloride Cl—CO—CO—Cl. For example, Bzl-O—CO—CO—Cl and n-Bu—O—CO—CO—Cl are prepared by reaction of respectively benzyl alcohol and butanol with oxalyl chloride in yields of 50% and 80% [Warren, C. B., and Malee, E. J., J. Chromatography 64, 219–222 (1972); incorporated herein by reference].

Ketoamides $M_1$-AA-CO—$NR_3R_4$, M-AA-AA-CO—$NR_3R_4$, M-AA-AA-AA-CO—$NR_3R_4$, M-AA-AA-AA-AA-CO—$NR_3R_4$ were prepared indirectly from the ketoesters. The ketone carbonyl group was first protected as shown in the following scheme and then the ketoamide was prepared by reaction with an amine H—$NR_3R_4$. The illustrated procedure should also work with other protecting groups. In addition, the corresponding ketoacid could be used as a precursor. Blocking the ketone carbonyl group of the ketoacid and then coupling with an amine H—$NR_3R_4$ using standard peptide coupling reagents would yield an intermediate which could then be deblocked to form the ketoamide.

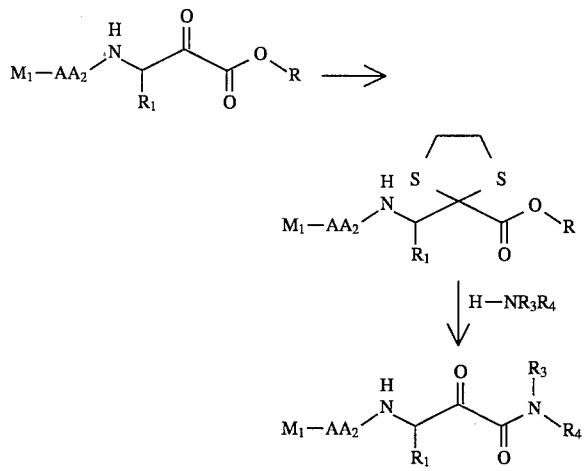

The following detailed examples are given to illustrate the invention and are not intended to limit it in any manner.

EXAMPLE 1

Z-Leu-Phe-CONH-Et

To a stirred solution of Z-Leu-Phe-OH (20 g, 48.5 mmole), 4-dimethylaminopyridine (0.587 g, 4.8 mmole), and pyridine (15.7 ml, 194 mmole) in anhydrous THF (100 ml) was added ethyl oxalyl chloride (11.4 ml, 101.8 mmole) at a rate sufficient to initiate refluxing. The mixture was gently refluxed for 4 hours, cooled to room temperature, and water (80 ml) was added. The reaction mixture was stirred vigorously for 30 rain, and extracted with ethyl acetate (3×100 ml). The combined organic layers were washed with water (2×100 ml), saturated sodium chloride (2×100 ml), decolorized with decolorizing carbon, dried over magnesium sulfate, and concentrated, leaving a dark orange oil. Chromatography on a silica gel column with $CHCl_3/CH_3OH$ (50:1 v/v) afforded 14.63 g (y=53%) of Z-Leu-Phe-enolester. The product was a yellow oil. Single spot on TLC, $R_f$=0.77 ($CHCl_3/CH_3OH$ 50:1). NMR ($CDCl_3$) ok.

To a stirred pale yellow solution of the Z-Leu-Phe-enolester (14.63 g, 25.73 mmole) in anhydrous ethanol (50 ml) was added a solution of sodium ethoxide (0.177 g, 2.6 mmole) in ethanol (5 ml). The orange solution was stirred for 3 hours at room temperature, then the ethanol was evaporated and the residue was treated with ethyl ether (300 ml). The ether layer was washed with water (2×100 ml), saturated sodium chloride (2×100 ml), dried over magnesium sulfate, and concentrated, leaving a orange oil. Chromatography on a silica gel column with $CHCl_3/CH_3OH$ (50:1 v/v) afforded 7.76 g (y=64%) of the α-ketoester Z-Leu-Phe-COOEt. The product was a yellow oil. Single spot on TLC, $R_f$=0.44 ($CHCl_3/CH_3OH$ 50:1). NMR ($CDCl_3$) ok. MS (FAB, calcd. for $C_{26}H_{32}N_2O_6$: 468.6), m/e=469 (M+1).

The α-carbonyl group of Z-Leu-Phe-COOEt was protected by the following procedure. To a solution of Z-Leu-Phe-COOEt (1 g, 2.13 mmole) in 5 ml of $CH_2Cl_2$ was added 1,2-ethanedithiol (0.214 ml, 2.55 mmole), followed by 0.5 ml of boron trifluoride etherate. The solution was stirred overnight at room temperature. Water (20 ml) and ethyl ether (20 ml) were added. The organic layer was separated, washed with water (2×10 ml), saturated sodium chloride (2×10 ml), dried over magnesium sulfate, and evaporated to afford 0.98 g (y=84%) yellow semisolid.

The protected α-ketoester (0.98 g, 1.8 mmole) was dissolved in ethanol (5 ml), cooled to 0°–5° C. in an ice bath, and ethylamine was bubbled through the solution until 2.43 g (54 mmole) had been added. The reaction mixture was allowed to warm to room temperature slowly, and stirred overnight. The mixture was filtered, a white precipitate was removed, leaving a yellow semisolid. Chromatography on a silica gel column with $CHCl_3/CH_3OH$ (30:1 v/v) afford 0.63 g (y=75%) of Z-Leu-Phe-CONH-Et. The product was a pale yellow solid. Single spot on TLC, $R_f$=0.60 ($CHCl_3/CH_3OH$ 20:1); mp 145°–147° C. Anal. calcd. for $C_{26}H_{33}N_3O_5$: 467.56; C, 66.79; H 7.11; N,8.99; found: C, 66.59; H, 7.09; N, 8.95. NMR ($CDCl_3$) ok. MS (FAB) m/e=468 (M+1).

EXAMPLE 2

Z-Leu-Phe-CONH-nPr

This compound was synthesized from the protected α-ketoester and propylamine in 92% yield by the procedure described in Example 1. Single spot on TLC, $R_f$=0.50 ($CHCl_3/CH_3OH$ 50:1); mp 152°–153° C. Anal. calcd. for $C_{27}H_{35}N_3O_5$: 481.57; C, 67.33; H, 7.33; N, 8.72. Found: C, 67.21; H, 7.38; N, 8.64. NMR ($CDCl_3$) ok. MS (FAB) m/e=482 (M+1).

EXAMPLE 3

Z-Leu-Phe-CONH-nBu

This compound was synthesized from the protected α-ketoester and butylamine in 67% yield by the procedure described in Example 1. Single spot on TLC, $R_f$=0.50.($CHCl_3/CH_3OH$ 50:1); mp 152°–153° C. Anal. calcd. for $C_{28}H_{37}N_3O_5$: 495.59; C, 67.85; H, 7.52; N, 8.48. Found: C, 67.70; H, 7.57; N, 8.43. NMR ($CDCl_3$) ok. MS (FAB) m/e=496 (M+1).

EXAMPLE 4

Z-Leu-Phe-CONH-iBu

This compound was synthesized from the protected α-ketoester and isobutylamine in 53% yield by the procedure described in Example 1. Single spot on TLC, $R_f$=0.54 ($CHCl_3/CH_3OH$ 50:1); mp 152° C. Anal. calcd. for $C_{28}H_{37}N_3O_5$: 495.59; C, 67.85; H, 7.52; N, 8.48. Found: C, 67.77; H, 7.56; N, 8.40. NMR ($CDCl_3$) ok. MS (FAB) m/e=496 (M+1).

EXAMPLE 5

Z-Leu-Phe-CONH-Bzl

This compound was synthesized from the protected α-ketoester and benzylamine in 40% yield by the procedure described in Example 1. After reacting overnight, ethyl acetate (60 ml) was added. The mixture was filtered to remove a white precipitate. The solution was washed with cooled 1N HCl (3×25 ml), water (1×20 ml), saturated sodium chloride (2×20 ml), and dried over magnesium sulfate. The solution was evaporated leaving a yellow solid. Chromatography on a silica gel column with $CHCl_3/CH_3OH$ 30:1 v/v) afforded a yellow solid. Single spot on TLC, $R_f$=0.45 ($CHCl_3/CH_3OH$ 30:1); mp 160°–162° C. Anal. calcd. for $C_{31}H_{35}N_3O_5$: 529.61; C, 70.30; H, 6.66; N, 7.93. Found: C, 70.18; H, 6.67; N, 7.99. NMR ($CDCl_3$) ok. MS (FAB) m/e=530 (M+1).

EXAMPLE 6

Z-Leu-Phe-CONH-$(CH_2)_2$Ph

This compound was synthesized from the protected α-ketoester and phenethylamine in 50% yield by the procedure described in Example 5. Single spot on TLC, $R_f$=0.50 ($CHCl_3/CH_3OH$ 30:1); mp 151°–153° C. Anal. calcd. for $C_{32}H_{37}N_3O_5$: 543.66; C, 70.70; H, 6.86; N, 7.73. Found: C, 70.54; H, 6.88; N, 7.74. NMR ($CDCl_3$) ok. MS (FAB) m/e=544 (M+1).

EXAMPLE 7

Z-Leu-Abu-CONH-Et

This compound was synthesized from protected α-ketoester derived from Z-Leu-Abu-$CO_2$Et and ethylamine in 64% yield by the procedure described in Example 1. Single spot on TLC, $R_f$=0.36 ($CHCl_3/CH_3OH$ 50;1); mp 130°–132° C. Anal. calcd. for $C_{21}H_{31}N_3O_5$: 405.45; C, 62.20; H, 7.71; N, 10.36. Found: C, 61.92; H, 7.62; N, 10.31. NMR ($CDCl_3$) ok. MS (FAB) m/e=406 (M+1).

EXAMPLE 8

Z-Leu-Abu-CONH-nPr

This compound was synthesized from the corresponding protected α-ketoester and propylamine in 47% yield by the procedure described in Example 1. Single spot on TLC, $R_f$=0.28 ($CHCl_3/CH_3OH$ 50:1); mp 134°–135° C. Anal. calcd. for $C_{22}H_{33}N_3O_5$: 419.50; C, 62.98; H, 7.93; N, 10.02.

Found: C, 62.84; H, 7.97; N, 9.94. NMR (CDCl$_3$) ok. MS (FAB) m/e=420 (M+1).

EXAMPLE 9

Z-Leu-Abu-CONH-nBu

This compound was synthesized from the corresponding protected α-ketoester and butylamine in 42% yield by the procedure described in Example 1. Single spot on TLC, R$_f$=0.54 (CHCl$_3$/CH$_3$OH 50:1); mp 135°–136° C. Anal. calcd. for C$_{23}$H$_{35}$N$_3$O$_5$: 433.53; C, 63.71; H N, 9.69. Found: C, 63.48; H, 8.07; N, 9.67. NMR (CDCl$_3$) ok. MS (FAB) m/e=434 (M+1).

EXAMPLE 10

Z-Leu-Abu-CONH-iBu

This compound was synthesized from the corresponding protected α-ketoester and isobutylamine in 65% yield by the procedure described in Example 1. Single spot on TLC, R$_f$=0.25 (CHCl$_3$/CH$_3$OH 50:1); mp 133°–135° C. Anal. calcd. for C$_{23}$H$_{35}$N$_3$O$_5$: 433.52; C, 63.72; H, 8.14; N, 9.69. Found: C, 63.46; H, 8.10; N, 9.60. NMR (CDCl$_3$) ok. MS (FAB) m/e=434 (M+1).

EXAMPLE 11

Z-Leu-Abu-CONH-Bzl

This compound was synthesized from the corresponding protected α-ketoester and benzylamine in 29% yield by the procedure described in Example 5. Single spot on TLC, R$_f$=0.56 (CHCl$_3$/CH$_3$OH 30:1); mp 140°–141° C. Anal. calcd. for C$_{26}$H$_{33}$N$_3$O$_5$: 467.54; C, 66.79; H 7.11; N, 8.99. Found: C, 66.65; H, 7.07; N, 8.93. NMR (CDCl$_3$) ok. MS (FAB) m/e=468 (M+1).

EXAMPLE 12

Z-Leu-Abu-CONH-(CH$_2$)$_2$Ph

This compound was synthesized from the corresponding protected α-ketoester and phenethylamine in 51% yield by the procedure described in Example 5. Single spot on TLC, R$_f$=0.44 (CHCl$_3$/CH$_3$OH 30:1); mp 156°–157° C. Anal. calcd. for C$_{27}$H$_{35}$N$_3$O$_5$: 481.59; C, 67.34; H, 7.33; N, 8.72. Found: C, 67.38; H, 7.33; N, 8.78. NMR (CDCl$_3$) ok. MS (FAB) m/e=482 (M+1).

EXAMPLE 13

Z-Leu-Abu-CONH-(CH$_2$)$_3$—N(CH$_2$CH$_2$)$_2$O

This compound was synthesized from protected α-ketoester and 4(3-aminopropyl)morpholine in 33% yield by the procedure described in Example 1. After reacting overnight, ethyl acetate (80 ml) was added. The mixture was filtered to remove a white precipitate. The solution was washed with water (3×20 ml), saturated sodium chloride (2×20 ml), and dried over magnesium sulfate. The solution was evaporated leaving a yellow oil. Chromatography on a silica gel column with CHCl$_3$/CH$_3$OH (10:1 v/v) afforded a yellow semisolid, which was recrystallized from ethyl acetate/hexane to obtain a pale yellow solid. Single spot on TLC, R$_f$=0.42 (CHCl$_3$/CH$_3$OH 10:1); mp 125°–126° C. Anal. calcd. for C$_{26}$H$_{40}$N$_4$O$_6$: 504.63; C, 61.88; H, 7.99; N, 11.10. Found; C, 61,69; H, 7.95; N, 11.07. NMR (CDCl$_3$) ok. MS (FAB) m/e=505 (M+1).

EXAMPLE 14

Z-Leu-Abu-CONH—(CH$_2$)$_7$CH$_3$

This compound was synthesized from the corresponding protected α-ketoester and octylamine in 67% yield by the procedure described in Example 5. It was white solid. Single spot on TLC, R$_f$=0.55 (CHCl$_3$/CH$_3$OH 30:1); mp 134°–135° C. Anal. calcd. for C$_{27}$H$_{43}$N$_3$O$_5$: 489.66; C, 66.23; H, 8.85; N, 8.58. Found: C, 66.19; H, 8.81; N, 8.61. NMR (CDCl$_3$) ok. MS (FAB) m/e=490 (M+1).

EXAMPLE 15

Z-Leu-Abu-CONH-(CH$_2$)$_2$OH

This compound was synthesized from the corresponding protected α-ketoester and ethanolamine in 29% yield by the procedure described in Example 13. The product was a white sticky solid. Single spot on TLC, R$_f$=0.42 (CHCl$_3$/CH$_3$OH 10:1); mp 151°–153° C. Anal: calcd. for C$_{21}$H$_{31}$N$_3$O$_6$: 421.49; C, 59.84; H, 7.41; N, 9.97. Found: C, 59.11; H, 7.44; N, 9.81. NMR (CDCl$_3$) ok. MS (FAB) m/e=422 (M+1).

EXAMPLE 16

Z-Leu-Abu-CONH—(CH$_2$)$_2$O(CH$_2$)$_2$OH

This compound was synthesized from the corresponding protected α-ketoester and 2-(2-aminoethoxy)ethanol in 34% yield by the procedure described in Example 13. The product was white sticky solid. Single spot on TLC, R$_f$=0.42 (CHCl$_3$/CH$_3$OH 10:1); mp 103°–105° C. Anal.: calcd. for C$_{23}$H$_{35}$N$_3$O$_7$: 465.55; C, 59.34; H, 7.58; N, 9.03. Found: C, 59.23; H, 7.58; N, 9.01. NMR (CDCl$_3$) ok. MS (FAB) m/e=466 (M+1).

EXAMPLE 17

Z-Leu-Abu-CONH—(CH$_2$)$_{17}$CH$_3$

This compound was synthesized from the corresponding protected α-ketoester and octadecylamine in 12% yield by the procedure described in Example 5. The product was a pale yellow solid. Single spot on TLC, R$_f$=0.54 (CHCl$_3$/CH$_3$OH 30:1); mp 134°–136° C. Anal. calcd. for C$_{37}$H$_{63}$N$_3$O$_5$: 629.92; C, 70.55; H, 10.08; N, 6.67. Found: C, 70.71; H, 10.14; N, 6.75. NMR (CDCl$_3$) ok. MS (FAB) m/e=630.2 (M+1).

EXAMPLE 18

Z-Leu-Abu-CONH—CH$_2$—C$_6$H$_3$(OCH$_3$)$_2$

This compound was synthesized from the corresponding protected α-ketoester and 3,5-dimethoxybenzylamine in 45% yield by the procedure described in Example 5. The product was yellow sticky solid. Single spot on TLC, R$_f$=0.44 (CHCl$_3$/CH$_3$OH 30:1); mp 153°–155° C. Anal.: calcd. for C$_{28}$H$_{37}$N$_3$O$_7$: 527.62; C, 63.74; H, 7.07; N, 7.96. Found: C, 63.66; H, 7.09; N, 7.92. NMR (CDCl$_3$) ok. MS (FAB) m/e=528.8 (M+1).

EXAMPLE 19

Z-Leu-Abu-CONH—CH$_2$—C$_4$H$_4$N

This compound was synthesized from the corresponding protected α-ketoester and 4-(aminomethyl)pyridine in 45% yield by the procedure described in Example 13. The product was greenish yellow solid. Single spot on TLC, $R_f$=0.55 (CHCl$_3$/CH$_3$OH 10:1); mp 124°–126° C. Anal: calcd. for C$_{25}$H$_{32}$N$_4$O$_5$: 468.55; C, 64.08; H, 6.88; N, 11.96. Found: C, 63.88; H, 6.87; N, 11.96. NMR (CDCl$_3$) ok. MS (FAB) m/e=469 (M+1).

It is obvious that those skilled in the art may make modifications to the invention without departing from the spirit of the invention or the scope of the subjoined claims and their equivalents.

What is claimed is:

1. A peptide ketoamide compound of the formula:

M$_1$-AA$_2$-AARES—CO—NH—R$_4$ or a pharmaceutically acceptable salt, wherein

AARES represents AA$_1$,

M$_1$ represents H, NH$_2$—CO—, NH$_2$—CS—, NH$_2$—SO$_2$—, X—NH—CO—, X$_2$N—CO—, X—NH—CS—, X$_2$N—CS—, X—NH—SO$_2$—, X$_2$N—SO$_2$—, X—CO—, X—CS—, X—SO$_2$—, X—O—CO—, or X—O—CS—;

X is selected from the group consisting of C$_{1-10}$ alkyl, C$_{1-10}$ fluoroalkyl, C$_{1-10}$ alkyl substituted with J, C$_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C$_{1-10}$ alkyl with an attached phenyl group, C$_{1-10}$ alkyl with two attached phenyl groups, C$_{1-10}$ alkyl with an attached phenyl group substituted with K, C$_{1-10}$ alkyl with two attached phenyl groups substituted with K, C$_{1-10}$ alkyl with an attached phenoxy group, and C$_{1-10}$ alkyl with an attached phenoxy group substituted with K on the phenoxy group;

J is selected from the group consisting of halogen, COOH, OH, CN, NO$_2$, NH$_2$, C$_{1-10}$ alkoxy, C$_{1-10}$ alkylamine, C$_{2-12}$ dialkylamine, C$_{1-10}$ alkyl-O—CO—, C$_{1-10}$ alkyl-O—CO—NH—, and C$_{1-10}$ alkyl-S—;

K is selected from the group consisting of halogen, C$_{1-10}$ alkyl, C$_{1-10}$ perfluoroalkyl, C$_{1-10}$ alkoxy, NO$_2$, CN, OH, CO$_2$H, amino, C$_{1-10}$ alkylamino, C$_{2-12}$ dialkylamino, C$_1$-C$_{10}$ acyl, C$_{1-10}$ alkoxy-CO—, and C$_{1-10}$ alkyl-S—;

AA$_2$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-1-napthyl)-COOH, NH$_2$CH(CH$_2$-2-naphthyl)-COOH, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, trifluoroleucine, and hexafluoroleucine;

AA$_1$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-1-napthyl)-COOH, NH$_2$CH(CH$_2$-2-napthyl)-COOH, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, trifluoroleucine, and hexafluoroleucine; and R$_4$ is selected from the group consisting of C$_{3-20}$ cyclized alkyl with an attached phenyl group, C$_{1-20}$ alkyl with an attached phenyl group substituted with K, C$_{1-20}$ alkyl with an attached phenyl group disubstituted with K, C$_{1-20}$ alkyl with an attached phenyl group trisubstituted with K, C$_{3-20}$ cyclized alkyl with an attached phenyl group substituted with K, C$_{1-10}$ alkyl with a morpholine ring attached through nitrogen to the alkyl, C$_{1-10}$ alkyl with a piperidine ring attached through nitrogen to the alkyl, C$_{1-10}$ alkyl with a pyrrolidine ring attached through nitrogen to the alkyl, C$_{1-20}$ alkyl with an OH group attached to the alkyl, —CH$_2$CH$_2$OCH$_2$CH$_2$OH, C$_{1-10}$ alkyl with an attached 4-pyridyl group, C$_{1-10}$ alkyl with an attached 3-pyridyl group, C$_{1-10}$ alkyl with an attached 2-pyridyl group, —NH—CH$_2$CH$_2$-(4-hydroxyphenyl), and —NH—CH$_2$CH$_2$-(3-indolyl).

2. A peptide ketoamide compound for inhibiting serine and cysteine proteases selected from the group consisting of:

(a) Z-Leu-Phe-CONH—(CH$_2$)$_2$Ph,
(b) Z-Leu-Abu-CONH—(CH$_2$)$_2$Ph,
(c) Z-Leu-Abu-CONH—(CH$_2$)$_3$—N(CH$_2$CH$_2$)$_2$O (morpholino),
(d) Z-Leu-Abu-CONH—(CH$_2$)$_7$CH$_3$,
(e) Z-Leu-Abu-CONH—(CH$_2$)$_2$OH,
(f) Z-Leu-Abu-CONH—(CH$_2$)$_2$O(CH$_2$)$_2$OH,
(g) Z-Leu-Abu-CONH—(CH$_2$)$_{17}$CH$_3$,
(h) Z-Leu-Abu-CONH—CH$_2$—C$_6$H$_3$(OCH$_3$)$_2$ (3,5 dimethoxy); and
(i) Z-Leu-Abu-CONH—CH$_2$—C$_4$H$_4$N (4-pyridyl).

3. A peptide ketoamide compound of the formula:

M$_1$-AA$_2$-AARES—CO—NH—R$_4$ or a pharmaceutically acceptable salt, wherein

AARES represents AA$_1$,

M$_1$ represents H, NH$_2$—CO—, NH$_2$—CS—, NH$_2$—SO$_2$—, X—NH—CO—, X$_2$N—CO—, X—NH—

CS—, $X_2$N—CS—, X—NH—$SO_2$—, $X_2$N—$SO_2$—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_{1-10}$ acyl, $C_{1-10}$ alkoxy-CO—, and $C_{1-10}$ alkyl-S—;

$AA_2$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—COOH, alpha-aminoheptanoic acid, $NH_2$—CH($CH_2$-1-napthyl)-COOH, $NH_2$—CH($CH_2$-2-naphthyl)-COOH, $NH_2$—CH($CH_2$-cyclohexyl)-COOH, $NH_2$—CH($CH_2$-cyclopentyl)-COOH, $NH_2$—CH($CH_2$-cyclobutyl)-COOH, $NH_2$—CH($CH_2$-cyclopropyl)-COOH, trifluoroleucine, and hexafluoroleucine;

$AA_1$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—COOH, alpha-aminoheptanoic acid, $NH_2$—CH($CH_2$-1-napthyl)-COOH, $NH_2$CH($CH_2$-2-napthyl)-COOH, $NH_2$—CH($CH_2$-cyclohexyl)-COOH, $NH_2$—CH($CH_2$-cyclopentyl)—COOH, $NH_2$—CH($CH_2$-cyclobutyl)-COOH, $NH_2$—CH($CH_2$-cyclopropyl)-COOH, trifluoroleucine, and hexafluoroleucine; and $R_4$ is selected from the group consisting of $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ alkyl with an attached 4-pyridyl group, $C_{1-10}$ alkyl with an attached 3-pyridyl group, $C_{1-10}$ alkyl with an attached 2-pyridyl group, —NH—$CH_2CH_2$-(4-hydroxyphenyl), and —NH—$CH_2CH_2$-(3-indolyl).

4. A peptide ketoamide compound of the formula:

$M_1$-$AA_2$-AARES-CO—NH—$R_4$ or a pharmaceutically acceptable salt, wherein

AARES represents $AA_1$, $M_1$ represents H, $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl-O—CO—, $C_{1-10}$ alkyl-O—CO—NH—, and $C_{1-10}$ alkyl-S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$–$C_{10}$ acyl, $C_{1-10}$ alkoxy-CO—, and $C_{1-10}$ alkyl-S—;

$AA_2$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—COOH, alpha-aminoheptanoic acid, $NH_2$—CH($CH_2$-1-napthyl)-COOH, NH$_2$CH(CH$_2$-2-napthyl)-COOH, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, trifluoroleucine, and hexafluoroleucine;

AA$_1$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-1-napthyl)-COOH, NH$_2$—CH(CH$_2$-2-napthyl)-COOH, NH$_2$—CH(CH$_2$-cyclohexyl)-COOH, NH$_2$—CH(CH$_2$-cyclopentyl)-COOH, NH$_2$—CH(CH$_2$-cyclobutyl)-COOH, NH$_2$—CH(CH$_2$-cyclopropyl)-COOH, trifluoroleucine, and hexafluoroleucine; and R$_4$ is selected from the group consisting of C$_{1-10}$ alkyl with a morpholine ring attached through nitrogen to the alkyl, C$_{1-10}$ alkyl with a piperidine ring attached through nitrogen to the alkyl, C$_{1-10}$ alkyl with a pyrrolidine ring attached through nitrogen to the alkyl, C$_{1-20}$ alkyl with an OH group attached to the alkyl, —CH$_2$CH$_2$OCH$_2$CH$_2$OH, C$_{1-10}$ alkyl with an attached 4-pyridyl group, C$_{1-10}$ alkyl with an attached 3-pyridyl group, C$_{1-10}$ alkyl with an attached 2-pyridyl group, —NH—CH$_2$CH$_2$-(4-hydroxyphenyl), and —NH—CH$_2$CH$_2$-(3-indolyl).

5. A peptide ketoamide compound for inhibiting serine and cysteine proteases selected from the group consisting of:

(a) Z-Leu-Abu-CONH—(CH$_2$)$_3$—N(CH$_2$CH$_2$)$_2$O(morpholino), (b) Z-Leu-Abu-CONH—(CH$_2$)$_2$OH, (c) Z-Leu-Abu-CONH—(CH$_2$)$_2$O(CH$_2$)$_2$OH, (d) Z-Leu-Abu-CONH—CH$_2$—C$_6$H$_3$(OCH$_3$)$_2$, and (e) Z-Leu-Abu-CONH—CH$_2$—C$_4$H$_4$N (2-pyridyl).

* * * * *